United States Patent
Beyer et al.

(10) Patent No.: US 6,881,218 B2
(45) Date of Patent: Apr. 19, 2005

(54) BLOOD CLOT FILTER

(75) Inventors: Ted Beyer, Queensbury, NY (US); William M. Appling, Granville, NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 10/138,152

(22) Filed: May 1, 2002

(65) Prior Publication Data

US 2003/0208253 A1 Nov. 6, 2003

(51) Int. Cl.[7] .............................................. A61M 29/00
(52) U.S. Cl. ..................................... 606/200; 606/198
(58) Field of Search ................................ 606/200, 198, 606/113, 114, 127, 157; 623/112

(56) References Cited

U.S. PATENT DOCUMENTS

| | | | | |
|---|---|---|---|---|
| 4,425,908 A | * | 1/1984 | Simon ........................ 128/899 |
| 4,580,568 A | | 4/1986 | Gianturco | |
| 5,350,398 A | * | 9/1994 | Pavcnik et al. ............. 606/200 |
| 5,383,887 A | * | 1/1995 | Nadal ......................... 606/200 |
| 5,549,626 A | | 8/1996 | Miller et al. | |
| 6,099,549 A | | 8/2000 | Bosma et al. ............... 606/200 |
| 6,241,746 B1 | | 6/2001 | Bosma et al. | |
| 6,267,776 B1 | * | 7/2001 | O'Connell ................... 606/200 |
| 6,267,777 B1 | | 7/2001 | Bosma et al. ............... 606/200 |
| 6,443,972 B1 | | 9/2002 | Bosma et al. ............... 606/200 |
| 6,582,447 B1 | * | 6/2003 | Patel et al. .................. 606/200 |
| 6,702,834 B1 | * | 3/2004 | Boylan et al. .............. 606/200 |

* cited by examiner

Primary Examiner—Paul B. Prebilic
(74) Attorney, Agent, or Firm—Reed Smith LLP

(57) ABSTRACT

The filter is composed of two portions. A first portion is a set of zi-zag struts arranged in a cylindrical fashion which fit against the wall of the vascular lumen and provide a base for positioning a filter portion. A filter portion is a set of struts. Each filtering strut has its upstream end connected to the positioning portion at the vascular wall and its downstream end held at a central position in the vascular lumen by a frangible connector or cord.

The central connector has a center opening to permit blood flow through the central opening. When the cord is cut, the resilient filter struts flex radially outward against the vascular wall in a parked condition to provide a non-filtered state without requiring removal of the filter from the patient.

17 Claims, 3 Drawing Sheets

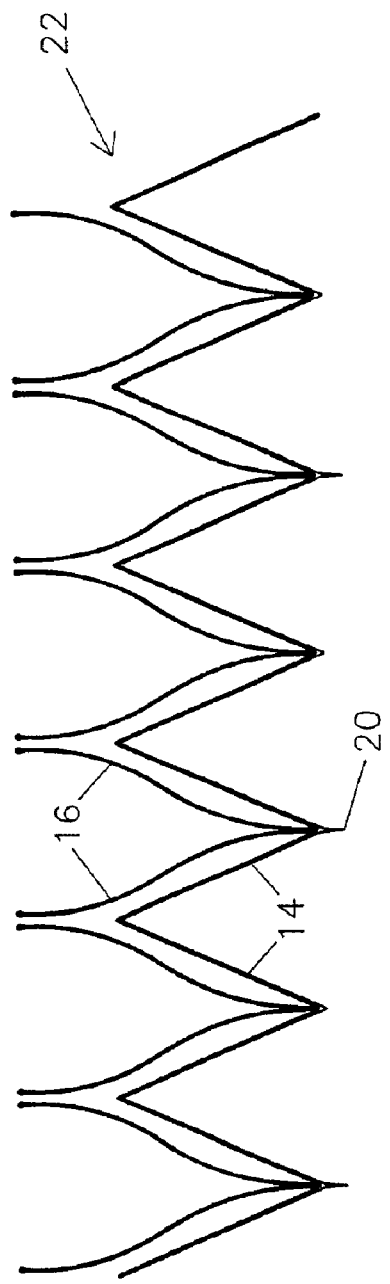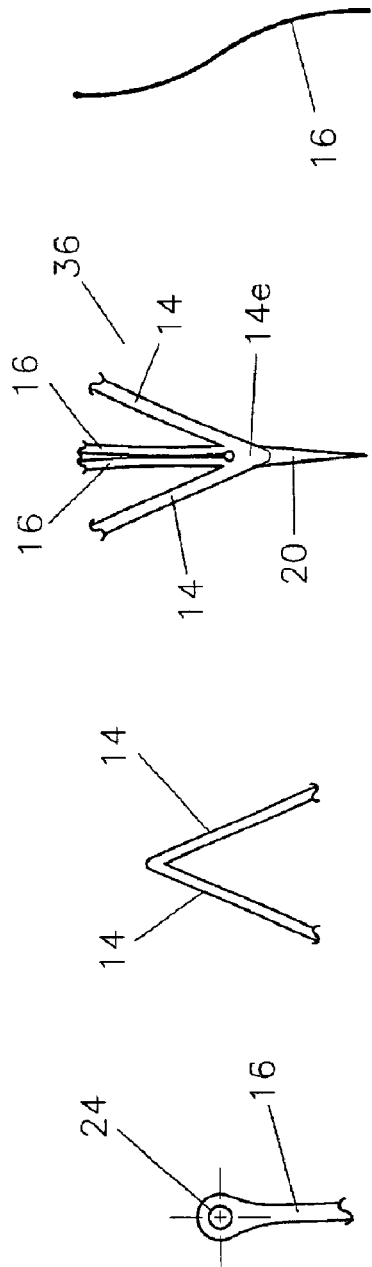

BLOOD CLOT FILTER

BACKGROUND OF THE INVENTION

This invention relates in general to a blood clot filter and more particularly to one that can be inactivated without being removed from the vascular lumen.

Blood clot filters of the type disclosed herein are normally deployed in the inferior vena cava. It is known in the art to have permanent blood clot filters, temporary blood clot filters and blood clot filters which can be converted from being a filter to a non-filtered state without requiring removal thereof.

There are known advantages and drawbacks to each of these three types of filters and each has its appropriate role.

A large number of different blood clot filter designs are known for various techniques that provide various degrees of centering, filter efficiency, blood flow characteristics and ease or difficulty of removal. Certain filters are designed so that the filter can be left in the patient when the filtering function is no longer required.

Because the various desirable characteristics of a blood clot filter are partially contradictory or antagonistic toward one another, it is desired to provide a filter which has an optimum trade-off of the various desirable characteristics.

It is one purpose of this invention to provide a blood clot filter which can be placed into a disabled state and left in the patient when the filtering function is no longer required.

It is a related purpose of this invention to provide a blood clot filter that will be centered in its filter state.

It is a further purpose of this invention to provide the above two purposes in a design that provides an optimum trade-off of blood flow, filter efficiency and the structural tensions necessary to maintain the filter centered in its filtered state.

It is a further object of this invention to provide the above objections in a device which is relatively easy for the surgeon to implant at a desired site.

It is a further purpose of this invention to provide a filter design which will catch blood clots that pose a risk and that will do so in a fashion which minimizes the chance of having the blood clots accumulate and block the flow through of blood at the site.

BRIEF DESCRIPTION

In brief, the embodiment disclosed employs a multi-strut zig-zag cylindrical positioning portion that is adapted to sit against the wall of a vascular lumen. This positioning portion is composed of twelve struts in one embodiment.

The active portion of the filter involves a number of resilient struts. Each of these filter struts has a first end connected to one of the twelve struts of the positioning portion. Thus the first end of each filter strut is at the vascular lumen wall. A second end of each filter strut is held in a central position within the lumen by a frangible connecting element such as a piece of surgical string.

The connecting element has a small central opening so that the faster flowing blood at the center of the vascular lumen can pass through carrying small clots that do not create potential damage. This central opening also assures the blood flow will dissolve the clots caught by the filter.

When the connecting element that keeps one end of each of the filter struts centrally located is cut, the filtering struts spring out to lie against the wall of the lumen so that a filtering function is no longer performed. The filter can thus be parked in place without having to be removed from the patient.

BRIEF DESCRIPTION OF THE FIGURES

FIG. 1 illustrates the filter state of the filter with some of the structure removed for clarity.

FIG. 3 shows an intermediate fabrication condition in which positioning struts 14 and filter struts 16 have been cut out of a sheet of stainless steel prior to being formed into a cylindrical shape.

FIG. 3A is a larger scale view of the downstream end of each filter strut 16, showing a small opening 24 to accommodate the connecting element that holds that end of each filter strut near the center of the vascular lumen within which the filter is positioned.

FIG. 3B is a larger scale view of one end or corner of the zig-zag set of positioning struts 14 that constitute the positioning portion of the filter; which positioning portion lies against the vascular wall.

FIG. 3C is a larger scale illustration of the corner or end where two of the filter struts 16 join with two of the positioning struts 14 at the vascular wall. FIG. 3C also illustrates the barb 20 which is used to fasten the filter to the vascular wall.

FIG. 3D is a larger scale view of one of the filter struts 16.

DESCRIPTION OF THE PREFERRED EMBODIMENTS

Figure 1:
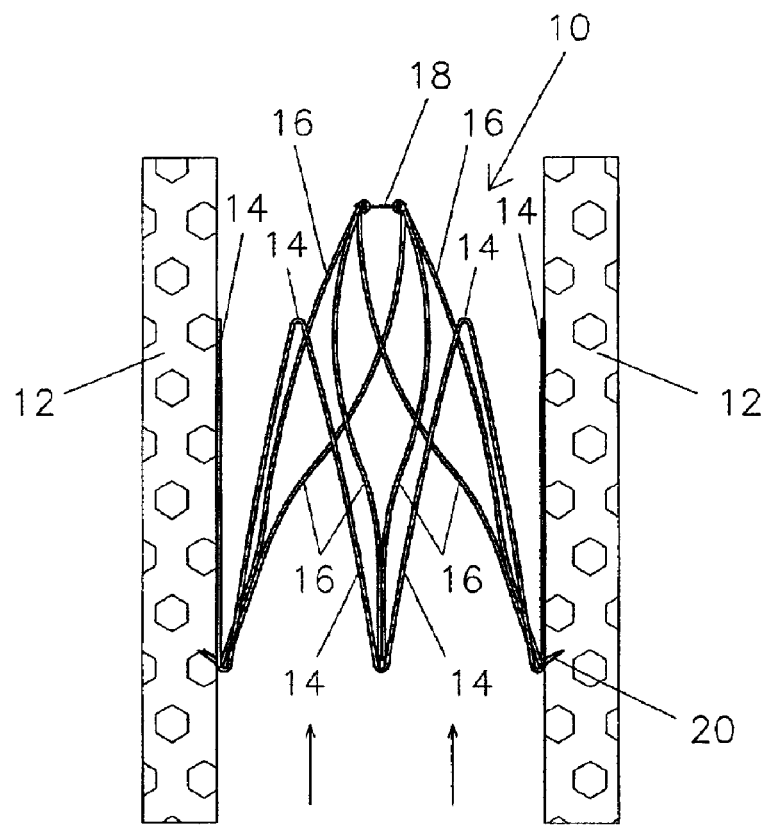
FIG. 1 is a schematic side view of an embodiment of the filter of this invention positioned in the wall of the vascular system.
Figure 2:
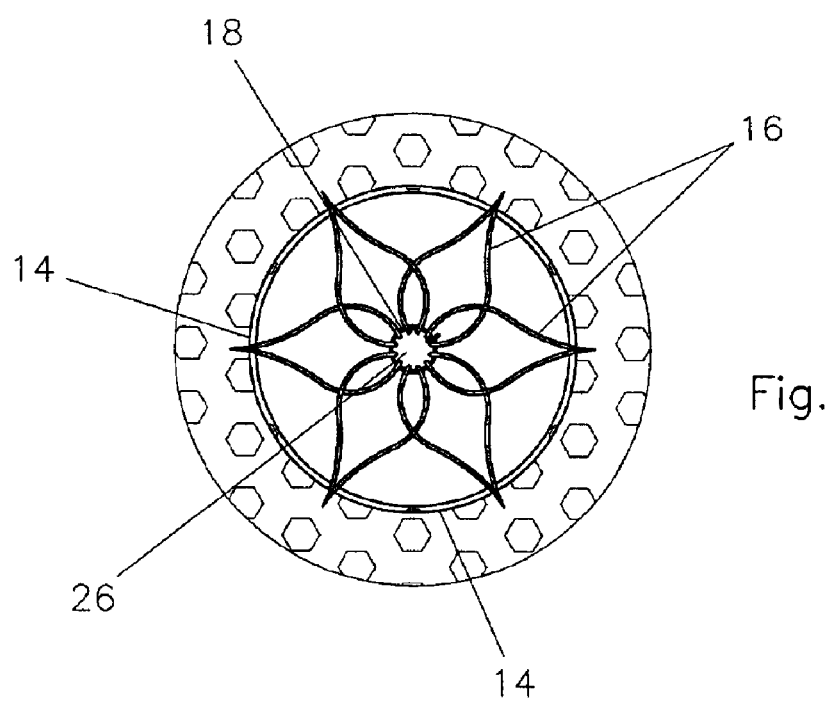
FIG. 2 is an end view of the FIG. 1 device in the deployed filter state.

The FIGS. all relate to the same embodiment. The self-centering blood clot filter 10 is shown in FIGS. 1 and 2 in its filter state. The filter 10 is deployed in a vascular lumen defined by a vascular wall 12. The filter is composed of a plurality of struts 14,16. Half of the struts are the struts 14 which are deployed in a zig-zag fashion against the inner surface of the vascular wall 12 to provide a positioning function. The other half are the struts 16 are deployed within the lumen to provide a blood clot filtering function. Thus the filter 10 has a multi-strut 14 positioning portion and a multi-strut 16 filtering portion.

More particularly, the set of positioning struts 14 have a zig-zag cylindrical deployment against the inner surface of the vascular wall 12. There are twelve positioning struts 14 in the embodiment shown.

In addition to the positioning struts, there are filter struts 16. There are twelve of these filter struts in the embodiment shown. Each filter strut 16 has one end (its upstream end) connected to one of the positioning struts 14. Each filter strut has a second end, a downstream end, held at a central portion of the vascular lumen by a frangible connector 18. The arrows in FIG. 1 show the direction of blood flow.

As can best be seen in FIGS. 3-3D, the positioning struts 14 are composed of a continuous strand of nitinol or stainless steel formed in a zig-zag pattern. At each upstream end 14e of two positioning struts 14, the ends of two filter struts 16 are connected.

As shown in FIG. 3, all of the struts 14 and 16 can be cut out of (by known laser techniques) a single sheet of material, which can be for example stainless steel or nitinol. A barb or hook 20, at the upstream end of three of the junctures 14e, provides an anchor which can attach the filter 10 to the vascular wall 12 so as to prevent migration of the filter 10. FIG. 3 illustrates an intermediate stage in the fabrication of the filter 10. The set of struts 14 and 16, as well as the barbs 20, are cut from a single sheet of material. When the intermediate product 22 is formed into a cylindrical element, both sets of struts; the filter struts 16, as well as the positioning struts 14, will define a cylindrical envelope.

The downstream end of each of the filter struts 16 has an eye 24, as shown in FIG. 3A. Through the twelve eyes 24, one for each of the twelve filter struts 16, a flexible cord 18 (which can be made of nylon or surgical thread) is threaded to pull the downstream ends of the filter struts 16 into the central position shown in FIGS. 1 and 2.

The struts 16 are made of material having resilience so that they are under tension when held in the central position by the connector 18. When desired by the physician involved, the connector 18 can be cut, which will cause each of the filter struts 16 to spring back against the wall and to assume a position in essentially the same cylindrical envelope as are the positioning struts 14. In this fashion, the filter function can be disabled without having to remove the filter from the patient.

Each of the downstream ends of each of the filter struts 16 has its own eye 24 and is independent of the downstream end of any other filter strut 16. This assures that when the connector 18 is broken, each strut 16 will flex radially outward against the inner surface of the vascular wall 12.

As can best be seen in FIG. 2, the thread like connector 18 provides an open zone 26 at the center of the vascular lumen. This minimizes trapping clots smaller than the size of the opening 26. Accordingly, the filter 10 can be designed to catch only clots greater than a certain size; which are clots that are deemed to be of greatest danger to the patient involved. In one embodiment, the opening 26 has a diameter of approximately three millimeters (3 mm).

A further advantage of having this central opening 26 is that this is the area where the blood flow is the fastest. The flow will tend to dissolve blood clots caught by the struts 16. Thus the filter 10 will catch blood clots in a fashion that minimizes the risk of blocking the flow of the patient's blood.

The filter struts 16 shown have a particular curved configuration as illustrated in FIG. 3D. This provides the partially overlapping arrangement shown in FIG. 2 and is presently preferred to provide optimum filter coverage for the number of struts involved. However, the shape of the filter struts 16 can be different than as shown. Experimentation might show optimization of strut configuration as a function of vascular diameter.

In operation, the set of positioning struts 14 provide a transmission of force on the filter struts 16 that resists any tendency of the set of filter struts 16 to tilt over to one side. Thus the set of positioning struts 14 provides a centering function for the set of filter struts 16.

In one particular embodiment, each of the struts 14 and 16 has a diameter of approximately nine mils (0.009 inches). In that embodiment, each of the positioning struts 14 is three centimeters and each of the filter struts 16 is approximately four centimeters. In that embodiment, the angle between positioning struts 14, at both the upstream and downstream ends, is 47° in the FIG. 3 intermediate fabrication condition.

Figure 4:
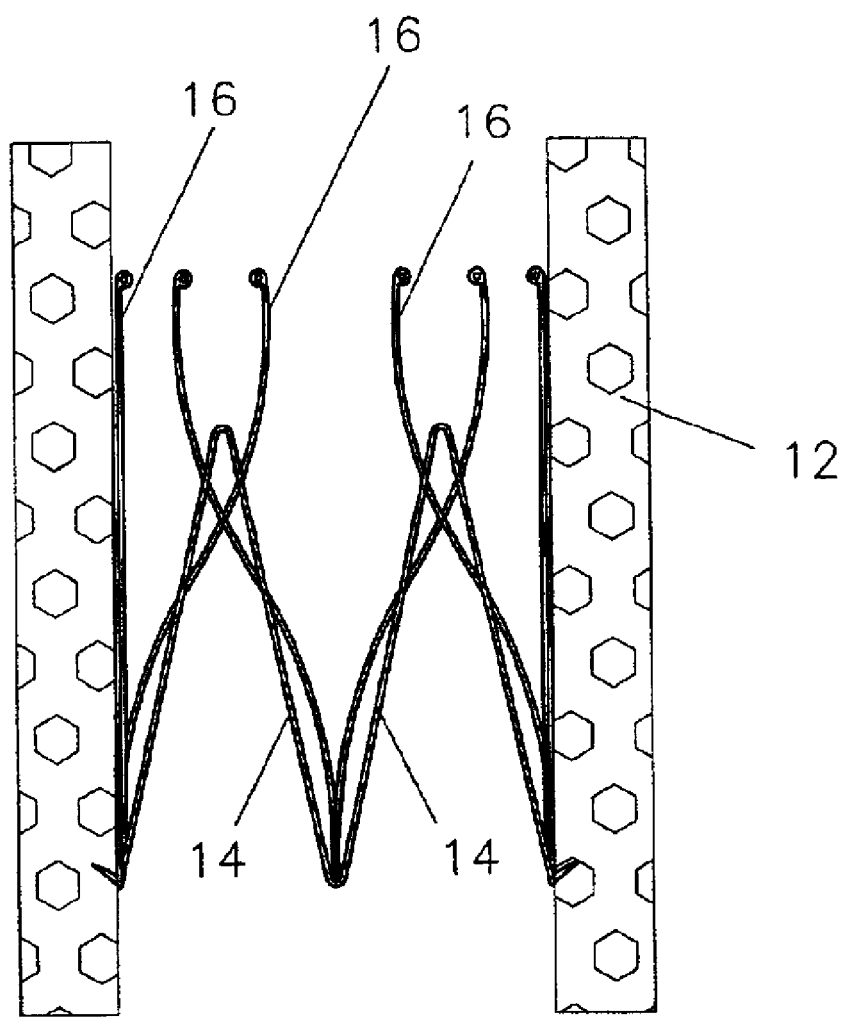
FIG. 4 is a schematic longitudinal sectional view of the FIG. 1 filter in the inactive state, after the connector 18 has been cut.

FIG. 4 illustrates the inactive state of the filter after the connecting element 18 has been cut. FIG. 4 shows the struts 16 parked against the wall of the lumen 12.

What is claimed is:

1. A self-centering blood clot filter having an active state and an inactive state for use in a vascular lumen comprising:
   a cylindrical positioning portion having a plurality of positioning struts adapted to sit against the wall of a vascular lumen, each of said positioning struts having an upstream end and a downstream end, pairs of said positioning struts having their upstream ends connected to provide a plurality of junctions,
   a filtering portion having a plurality of resilient filter struts, each of said filter struts having an upstream end and a downstream end,
   said upstream end of each of said filter struts being connected to a separate one of said plurality of junctions of the upstream ends of said positioning struts, this connection being the sole connection between said filter struts and said pairs of said positioning struts,
   a frangible connecting element connected to said downstream ends of said filter struts to maintain said downstream ends in a central location during the active state within a vascular lumen,
   said connecting element having a central opening during the active state to allow blood clots less than a predetermined size to pass through said opening near the center of a vascular lumen,
   said downstream ends of each of said filter struts being independently connected to said connecting element,
   the breaking of said frangible connector causing said resilient filter struts to flex radially outward against the wall of a vascular lumen to thereby create an inactive state for said filter.

2. The filter of claim 1 wherein: said connecting element is collapsible.

3. The filter of claim 1 wherein: said collapsible connecting element is a suture.

4. The filter of claim 1 wherein: said filter struts are paired, the upstream ends of each filter strut pair being connected to a separate one of said junctions of said positioning struts.

5. The filter of claim 4 wherein: said connecting element is collapsible.

6. The filter of claim 5 wherein: said collapsible connecting element is a suture.

7. The filter of claim 1 wherein: each of said filter struts is curved so that there is substantial overlap between adjacent filter struts in an axial projection.

8. The filter of claim 2 wherein: each of said filter struts is curved so that there is substantial overlap between adjacent filter struts in an axial projection.

9. The filter of claim 3 wherein: each of said filter struts is curved so that there is substantial overlap between adjacent filter struts in an axial projection.

10. The filter of claim 4 wherein: each of said filter struts is curved so that there is substantial overlap between adjacent filter struts in an axial projection.

11. The filter of claim 5 wherein: each of said filter struts is curved so that there is substantial overlap between adjacent filter struts in an axial projection.

12. The filter of claim 6 wherein: each of said filter struts is curved so that there is substantial overlap between adjacent filter struts in an axial projection.

13. The filter of claim 1 wherein: said positioning struts are arranged in a zig-zag fashion when deployed along the wall of a vascular lumen.

14. The filter of claim 2 wherein: said positioning struts are arranged in a zig-zag fashion when deployed along the wall of a vascular lumen.

15. The filter of claim 3 wherein: said positioning struts are arranged in a zig-zag fashion when deployed along the wall of a vascular lumen.

16. The filter of claim 12 wherein: said positioning struts are arranged in a zig-zag fashion when deployed along the wall of a vascular lumen.

17. A self-centering blood clot filter having an active state and an inactive state for use in a vascular lumen comprising:

a cylindrical positioning portion having a plurality of positioning struts adapted to sit against the wall of a vascular lumen, each of said positioning struts having an upstream end and a downstream end, a filtering portion having a plurality of resilient filter struts, each of said filter struts having an upstream end and a downstream end, said upstream ends of each of said filter struts being paired, each of said pairs being connected to a junction of the ends of a pair of said positioning struts, this connection being the sole connection between said filter struts and said pairs of positioning struts, each of said filter struts being curved so that when deployed, there is substantial overlap between adjacent struts in an axial projection, a frangible collapsible connecting element connected to said downstream ends of said filter struts to maintain said downstream ends in a central location within a vascular lumen, said connecting element having a central opening to allow blood clots less than a predetermined size to pass through said opening near the center of a vascular lumen, each of said downstream ends of each of said filter struts being independently connected to said connecting element, the breaking of said frangible connector causing said resilient filter struts to flex radially outward against the wall of a vascular lumen to thereby create an inactive state for said filter.

* * * * *